United States Patent [19]

Pao-Lang

[11] Patent Number: 6,080,111
[45] Date of Patent: Jun. 27, 2000

[54] WRIST ALARM APPARATUS FOR SUDDEN HEART ATTACK PATIENT

[76] Inventor: Li Pao-Lang, No. 532, Min-tzwu Rd., Lu Chou Hsiang, Taipei County, Taiwan

[21] Appl. No.: 09/025,798

[22] Filed: Feb. 19, 1998

[51] Int. Cl.[7] .................................................... A61N 5/00
[52] U.S. Cl. ........................................... 600/503; 600/500
[58] Field of Search ................................... 600/500–503, 600/300, 481–486; 128/897–899

[56] References Cited

U.S. PATENT DOCUMENTS

| | | | |
|---|---|---|---|
| 3,978,849 | 9/1976 | Geneen | 600/503 |
| 4,256,117 | 3/1981 | Percia et al. | 600/503 |
| 5,431,170 | 7/1995 | Mathews | 600/500 |
| 5,515,858 | 5/1996 | Myllymaki | 600/503 |
| 5,670,944 | 9/1997 | Myllymaki | 600/500 |
| 5,735,800 | 4/1998 | Yasukawa et al. | 600/502 |

*Primary Examiner*—Cary O'Connor
*Assistant Examiner*—Michael Astorino
*Attorney, Agent, or Firm*—Rosenberg, Klein & Lee

[57] ABSTRACT

A wrist alarm apparatus for use by a heart attack patient is provided that includes a maximum button and a minimum button laterally disposed on a housing part to respectively enter a maximum pulse rate limit and minimum pulse rate limit of a patient in a pre-set circuit for comparison with a patient's detected pulse rate in a comparator. An alarm device will produce a warning alarm, if the patient's pulse is equal to or higher than the maximum pulse rate limit or lower than the minimum pulse rate limit, to warn the patient or a nurse to take whatever actions are necessary.

1 Claim, 2 Drawing Sheets

WRIST ALARM APPARATUS FOR SUDDEN HEART ATTACK PATIENT

FIELD OF THE INVENTION

The present invention refers to a wrist alarm apparatus for sudden heart attack patient, in particularly characterized by giving warning alarm or phonetic sound asking for help when the heartbeats of a patient reach the maximum or minimum limit predetermined in accordance with the patient's physical condition, avoiding any delay for sending to hospital or untaking action of fist aid.

BACKGROUND OF THE INVENTION

In general, when a patient has heart attack, it may cause fatal danger if there is no prompt action such as taking medicine or sending to hospital. When it occurs in the living room or bedroom without being noticed in time, a regretful sudden death may enuse from delay for first aid or any appropriate actions.

OBJECTS OF THE INVENTION

The main object of the present invention is to solve above described problem by providing a wrist alarm apparatus for sudden heart attack patient pre-setting heartbeat maximum and minimum limits in accordance with the patient's condition and reminding the patient to take medicine by warning alarm when the patient's heartbeats reach the pre-setted limits preventing from having heart attack .

Further, the present invention is aimed to pre-set heartbeat limits in accordance with the patient's condition and call for attention to send the patient to hospital for first aid by phonetic sound asking for help when the patient's heartbeats reach the pre-set limit

DETAILED DESCRIPTION OF THE INVENTION

Other objects and the structure of the present invention will be apparent by following description with reference to the drawings.

Figure 1:
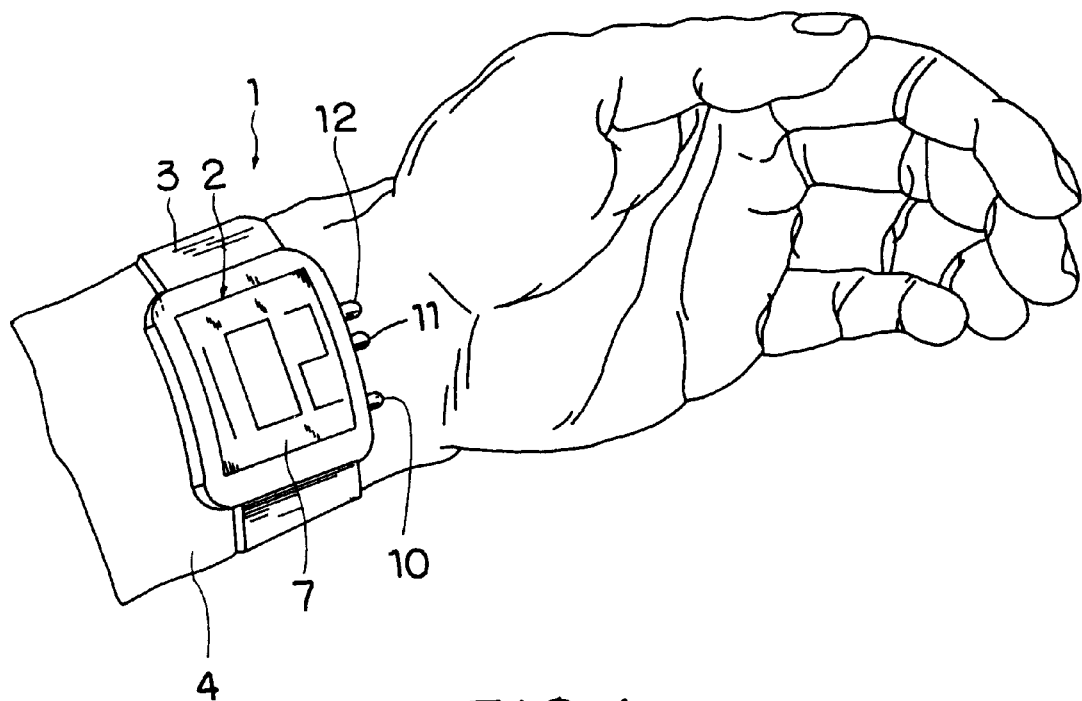
FIG. 1 shows the front view of this invention being worn on wrist.
Figure 2:
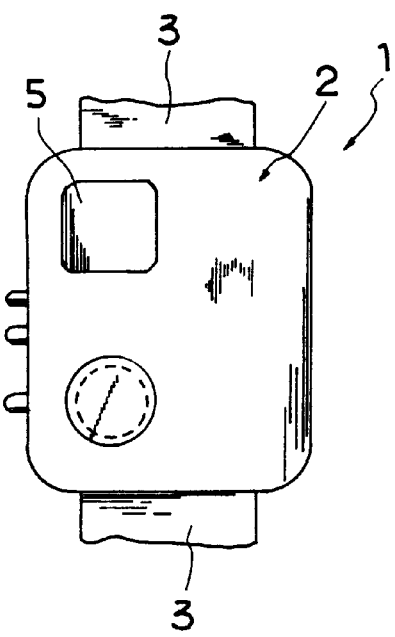
FIG. 2 shows the rear view of this invention.
Figure 3:
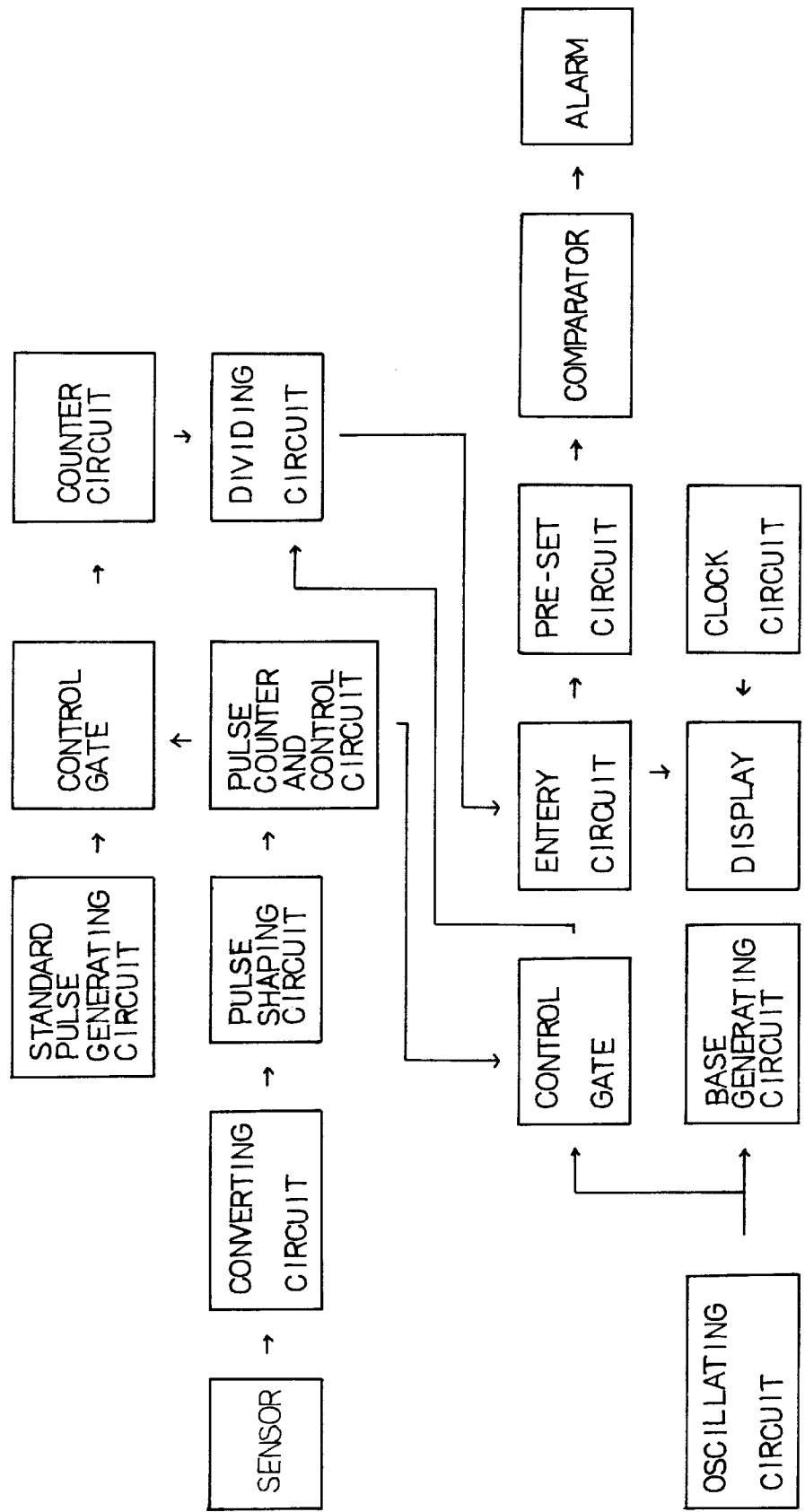
FIG. 3 shows the circuit of this invention.

Now refers to FIG. 1 to FIG. 3 showing a alarm device (1) connected with an integral control circuit and disposed in a housing part (2), like a wrist watch, fastened to inside of wrist (4) by a fastening belt (3), and detect the pulse from the wrist (4) by a sensor (5) set on the back side of said housing part (2), showing detected heartbeats per minute by three-digit number on a display screen (7) of a display device (6) in the front for user's observation. Wherein the patient's pulse is detected from the wrist (4) and then conveyed into the housing part (2), converted to electronic signal by energy converting circuit (8); electric pulse is formed by an oscillating circuit (9) at a pre-set frequency, then is counted through the energy converting circuit (8) and oscillating circuit (9) once the pulse is detected. Lastly, by a counter circuit the electric pulse is converted to form of speed of pulse, showed by three-digit number on the display screen (7) of the display device (6) representing the pulse per minute for user's observation.

Along one lateral of the housing part (2) of the present invention are start button (10), maximum button (11), and minimum button (12). In which the start button (10) refers to a button to start the integral circuit operation; one minute after pressing said start button (10) user's heartbeats begin to reveal every one minute, which in normal case is approximate 72 beats per minute.

Said maximum button (11) refers to a button which is pressed to record a pulse maximum limit in accordance with the patient's condition in a recorder of an internal pre-set circuit (13); by releasing said button (11) after setting numbers on the display screen (7) the pulse number is saved in the recorder of the internal pre-set circuit (13) for comparison with a detected pulse in an internal comparator (14) which may trigger an internal alarm (15) once the patient's detected pulse is equal to or higher than the pre-set maximum limit to give alarm signal, which may be alarm sound or phonetic sound, for the patient's or nurse's attention to take prompt necessary actions. Said minimum button (12) refers to a button for recording a pulse minimum limit in accordance with the patient's condition, having same pre-set process with said maximum button (11), the pulse minimum limit is saved in the recorder of the internal pre-set circuit (13) for comparison with a detected pulse in said intern a comparator (14) which may trigger the alarm (15) once the patient's detected pulse is equal or lower than the pre-set minimum limit to give alarm signal warning the patient or nurse to take prompt necessary actions.

I claim:

1. A wrist alarm apparatus for a heart attack patient, comprising:

a housing having opposing front and rear sides, said housing being secured to a heart attack patient's wrist by a fastening belt;

a heartbeat sensor disposed on said rear side of said housing in contiguous contact with the heart attack patient's wrist for detecting the user's heartbeats;

a display mounted to said front side of said housing for constantly indicating the heart attack patient's detected heart rate; and, a control circuit disposed within said housing and having an input coupled to said heartbeat sensor and an output coupled to said display, said control circuit including (a) a circuit coupled to said heartbeat sensor for counting a number of heartbeats detected thereby, (b) a circuit coupled to said counting circuit for converting said heartbeat count to a detected heart rate, (c) a single pre-set circuit for storing both maximum and minimum heart rate limits therein, said single pre-set circuit being coupled to a pair of switches, one of said pair of switches enabling entry of said maximum heart rate limit and the other of said pair of switches enabling entry of said minimum heart rate limit, (d) a single comparator coupled to said single pre-set circuit for comparing said detected heart rate with both said maximum heart rate limit and said minimum heart rate limit, and (e) a single alarm having an input coupled to an output of said single comparator for indicating both a detected heart rate equal to or beyond one of said maximum heart rate limit and a detected heart rate equal to or beyond said minimum heart rate limit, said single alarm being adapted to generate an audible signal.

* * * * *